US012239805B2

(12) United States Patent
Yamaguchi et al.

(10) Patent No.: US 12,239,805 B2
(45) Date of Patent: Mar. 4, 2025

(54) SPINAL DRAINAGE KIT CONTAINER

(71) Applicants: National University Corporation Hokkaido University, Hokkaido (JP); UNISIS Corporation, Tokyo (JP)

(72) Inventors: Shigeru Yamaguchi, Sapporo (JP); Hideya Saito, Tokyo (JP); Akihiro Saruya, Saitama (JP); Yoshikazu Matsumoto, Tokyo (JP); Kenta Kamiyama, Nagareyama (JP)

(73) Assignees: NATIONAL UNIVERSITY CORPORATION HOKKAIDO UNIVERSITY, Hokkaido (JP); UNISIS CORPORATION, Tokyo (JP)

( * ) Notice: Subject to any disclaimer, the term of this patent is extended or adjusted under 35 U.S.C. 154(b) by 519 days.

(21) Appl. No.: 17/291,108

(22) PCT Filed: Oct. 15, 2019

(86) PCT No.: PCT/JP2019/040387
§ 371 (c)(1),
(2) Date: May 4, 2021

(87) PCT Pub. No.: WO2020/095628
PCT Pub. Date: May 14, 2020

(65) Prior Publication Data
US 2022/0001155 A1 Jan. 6, 2022

(30) Foreign Application Priority Data
Nov. 9, 2018 (JP) ................. 2018-004349

(51) Int. Cl.
*B65D 1/26* (2006.01)
*A61M 27/00* (2006.01)
*B65D 75/32* (2006.01)

(52) U.S. Cl.
CPC ............... *A61M 27/00* (2013.01); *B65D 1/26* (2013.01); *B65D 75/32* (2013.01); *A61M 2209/06* (2013.01); *A61M 2210/1003* (2013.01)

(58) Field of Classification Search
CPC ......... B65D 1/26; B65D 43/163; B65D 75/32
See application file for complete search history.

(56) References Cited

U.S. PATENT DOCUMENTS 5,629,060 A * 5/1997 Garwood ................ B65B 7/168
156/581
7,624,859 B1 * 12/2009 Casanova ............ B65D 75/245
53/484

(Continued)

FOREIGN PATENT DOCUMENTS

CN 202538022 11/2012
EP 2 644 148 3/2013

(Continued)

OTHER PUBLICATIONS

Extended European Search Report issued Nov. 27, 2021 in corresponding European Patent Application No. 19881246.3.

(Continued)

*Primary Examiner* — Ernesto A Grano
*Assistant Examiner* — Symren K Sanghera
(74) *Attorney, Agent, or Firm* — Wenderoth, Lind & Ponack, L.L.P.

(57) ABSTRACT

A spinal drainage kit container includes a body, lid, and hinge. The body includes a peripheral portion and a first grip configured to be gripped when the lid is to be opened. The first grip is at a first corner of the body, opposite the hinge, and has a first protrusion in a first direction. The lid includes a contact configured to come into contact with the peripheral portion when the lid is closed, and a second grip connected to the contact and configured to be gripped when the lid is (Continued)

to be opened. The second grip is at a second corner of the lid, which overlaps with the first corner when the lid is closed; and the second grip has a second protrusion that protrudes in a second direction orthogonal to the first direction and does not overlap with the body when the lid is closed.

3 Claims, 8 Drawing Sheets

(56) References Cited

U.S. PATENT DOCUMENTS

| | | | | |
|---|---|---|---|---|
| 9,586,746 | B2 * | 3/2017 | Persells | B65D 43/162 |
| 2003/0150770 | A1 * | 8/2003 | Campbell | B65D 43/162 |
| | | | | 206/722 |
| 2005/0109772 | A1 * | 5/2005 | Thorpe | B65D 81/3453 |
| | | | | 219/732 |
| 2009/0187116 | A1 | 7/2009 | Noishiki et al. | |
| 2011/0031154 | A1 * | 2/2011 | Overgaag | B65D 21/0217 |
| | | | | 206/509 |
| 2013/0264239 | A1 * | 10/2013 | Agrawal | B65D 85/00 |
| | | | | 53/457 |
| 2014/0110296 | A1 * | 4/2014 | Terzibashian | B65D 25/108 |
| | | | | 206/438 |
| 2018/0273254 | A1 * | 9/2018 | Hansen | B65D 43/0235 |
| 2020/0055642 | A1 * | 2/2020 | Barbier | B65D 43/0268 |
| 2021/0130060 | A1 * | 5/2021 | Goad | B65D 75/24 |

FOREIGN PATENT DOCUMENTS

| | | | | |
|---|---|---|---|---|
| JP | 2003-128106 | | 5/2003 | |
| JP | 2006-75275 | | 3/2006 | |
| JP | 2012-188131 | | 10/2012 | |
| JP | 2018-33562 | | 3/2018 | |
| WO | 94/08642 | | 4/1994 | |
| WO | 2005/096952 | | 10/2005 | |
| WO | 2014/049800 | | 4/2014 | |
| WO | WO-2014049800 | A1 * | 4/2014 | A61B 50/30 |

OTHER PUBLICATIONS

English Machine Translation of WO 2014/049800.
International Search Report issued Jan. 7, 2020 in International (PCT) Application No. PCT/JP2019/040387.

* cited by examiner

SPINAL DRAINAGE KIT CONTAINER

TECHNICAL FIELD

The present invention relates to a spinal drainage kit container.

BACKGROUND ART

Spinal drainage is a method in which a catheter is placed in a spinal subarachnoid space and spinal fluid and the like are drained out of the body for the purpose of improving pathological conditions such as a subarachnoid hemorrhage.

For example, WO 2005/96952 describes a method for harvesting bone marrow, comprising steps of forming a hole in cortical bone, inserting a flexible catheter into the hole, and aspirating bone marrow through the catheter.

SUMMARY OF INVENTION

Technical Problem

A spinal drainage kit used for the spinal drainage as described above is housed in a container. The container in which the spinal drainage kit is housed is preferably easy to open.

Solution to Problem

A spinal drainage kit container according to the invention includes:
- a container body provided with a recessed portion in which a spinal drainage kit that includes a catheter, a puncture needle for introducing the catheter into a living body, and a connector that is connected to the catheter is disposed;
- a lid; and
- a hinge connecting the container body and the lid,
- the container body including a peripheral portion provided at a periphery of the recessed portion, and a first grip portion that is connected to the peripheral portion and is gripped when the lid is to be opened;
- the first grip portion being provided at a first corner of the container body, which is opposite to the hinge;
- the first grip portion having a first protruding portion protruding in a first direction;
- the lid including a contact portion that comes into contact with the peripheral portion in a state where the lid is closed, and a second grip portion that is connected to the contact portion and is gripped when the lid is to be opened;
- the second grip portion being provided at a second corner of the lid, which overlaps with the first corner in plan view in the state where the lid is closed; and
- the second grip portion having a second protruding portion that protrudes in a second direction and does not overlap with the container body in plan view in the state where the lid is closed, the second direction being orthogonal to the first direction.

According to one aspect of the spinal drainage kit container, the first grip portion and the second grip portion may be separated from each other in the state where the lid is closed.

According to one aspect of the spinal drainage kit container, the container body may have a bottom portion that defines the recessed portion, and the bottom portion may have a projecting portion that defines a first chamber in which the catheter is disposed, a second chamber in which the puncture needle is disposed, and a third chamber in which the connector is disposed.

According to one aspect of the spinal drainage kit container, the second chamber and the third chamber may be surrounded by the first chamber in plan view.

According to one aspect of the spinal drainage kit container, the first chamber, the second chamber, and the third chamber may be connected to each other, and a groove that enables communication between the first chamber and an external space may be provided at the peripheral portion.

According to one aspect of the spinal drainage kit container, the groove may be provided at the first corner.

According to one aspect of the spinal drainage kit container, a material for the container body and the lid may be plastic.

DESCRIPTION OF EMBODIMENTS

Preferred embodiments of the invention are described in detail below with reference to the drawings. It is noted that the following embodiments do not unduly limit the scope of the invention as stated in the claims. In addition, all of the elements described in the following embodiments are not necessarily essential requirements of the invention.

1. Spinal Drainage Kit Container

Figure 1:
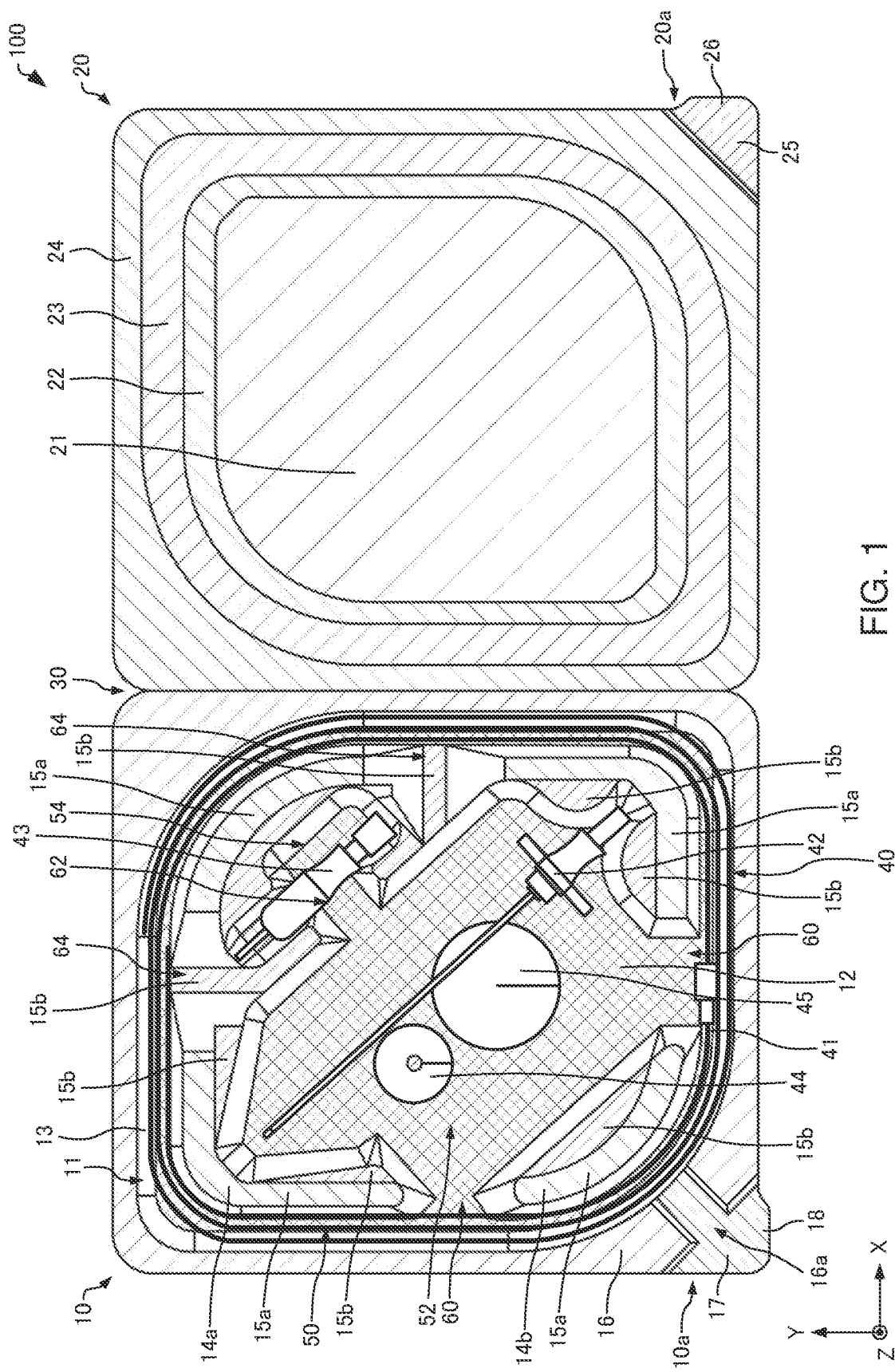
FIG. 1 is a plan view schematically illustrating a spinal drainage kit container according to the present embodiment.
Figure 2:
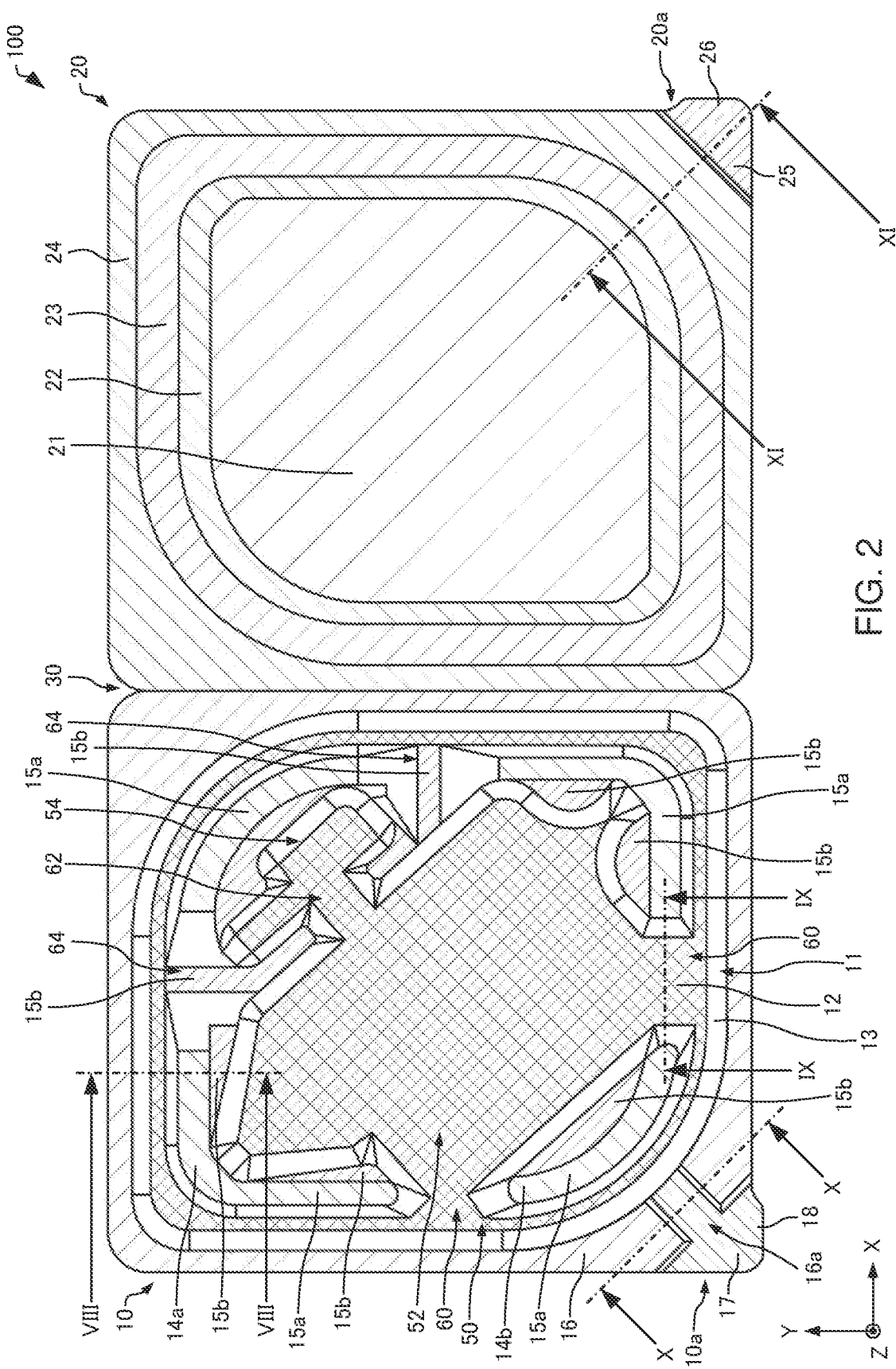
FIG. 2 is a plan view schematically illustrating the spinal drainage kit container according to the present embodiment.
Figure 3:
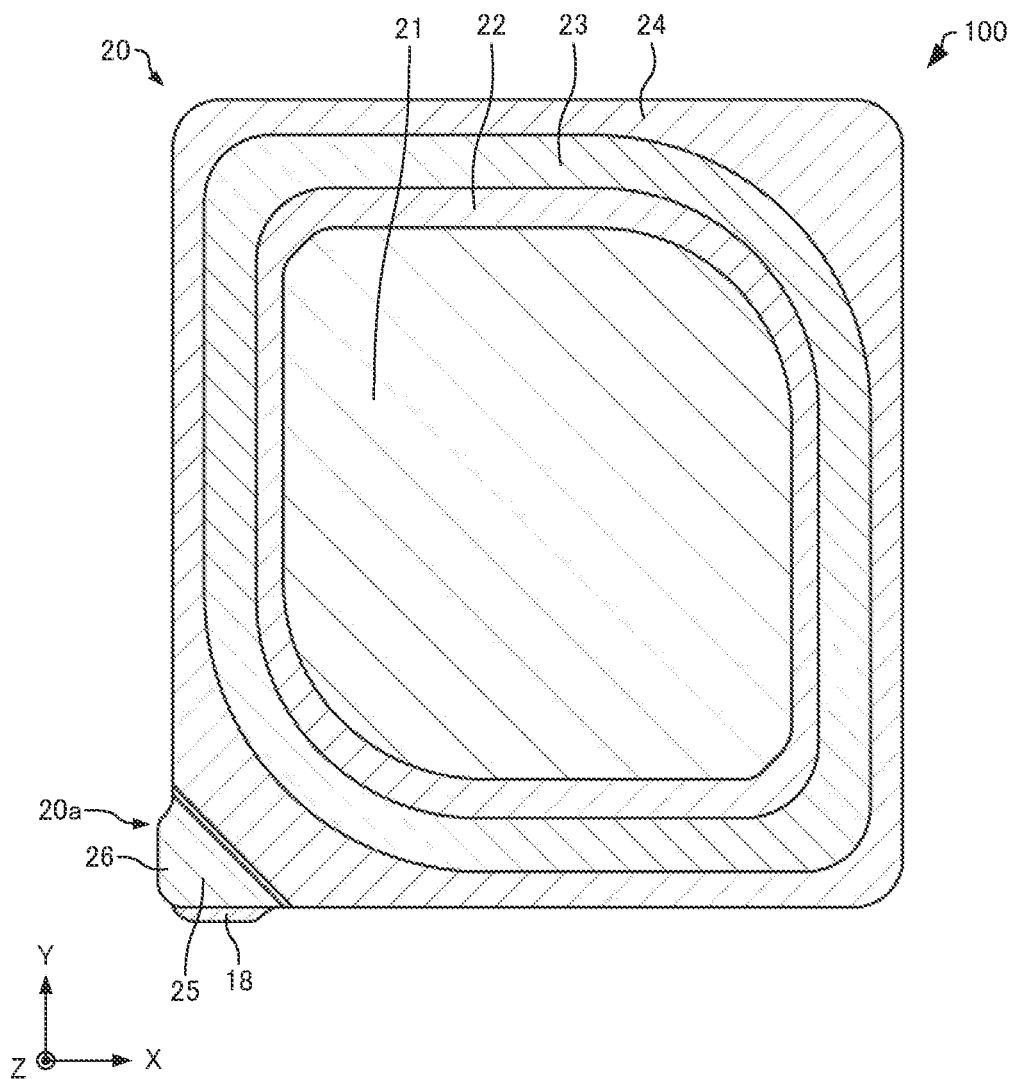
FIG. 3 is a plan view schematically illustrating the spinal drainage kit container according to the present embodiment.
Figure 4:
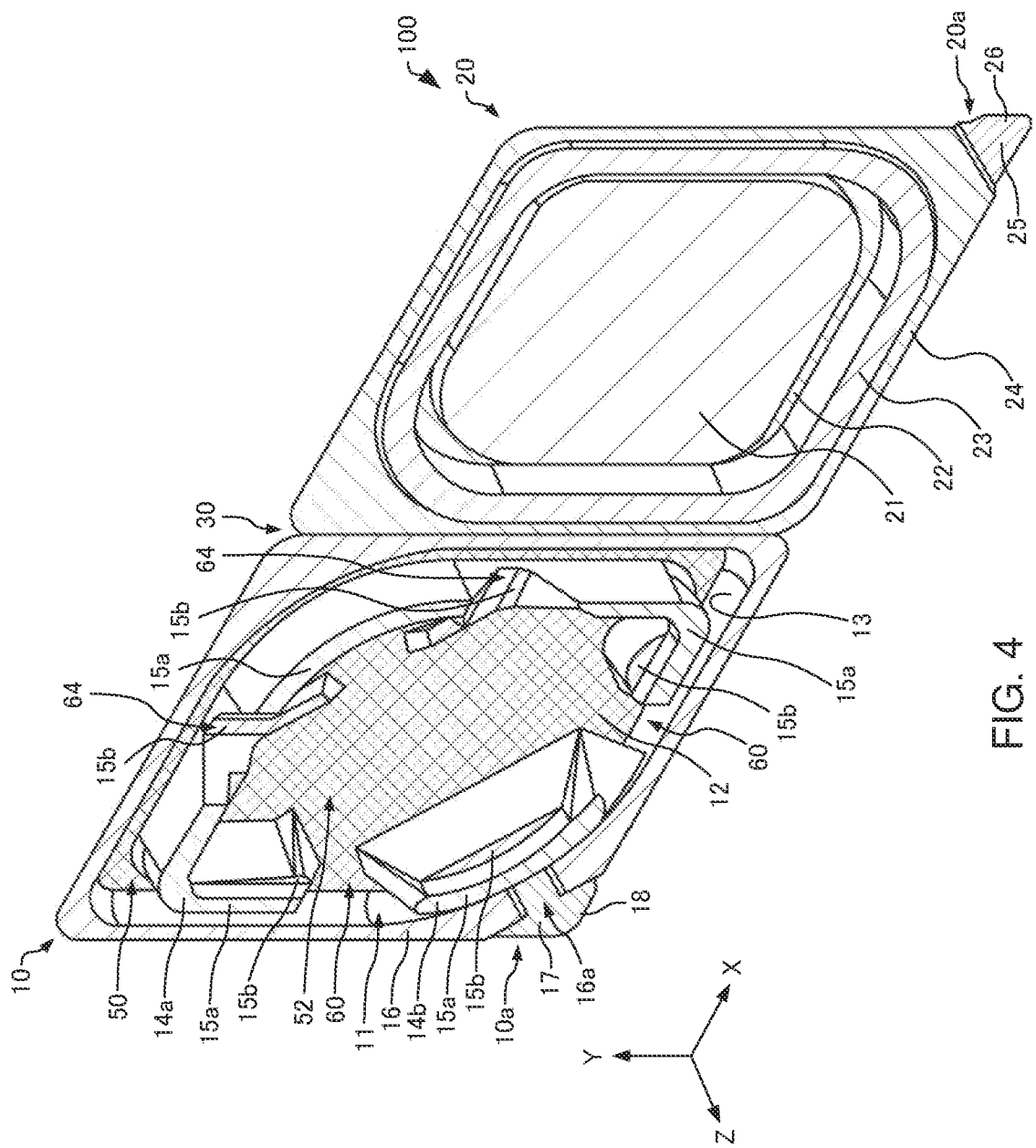
FIG. 4 is a perspective view schematically illustrating the spinal drainage kit container according to the present embodiment.
Figure 5:
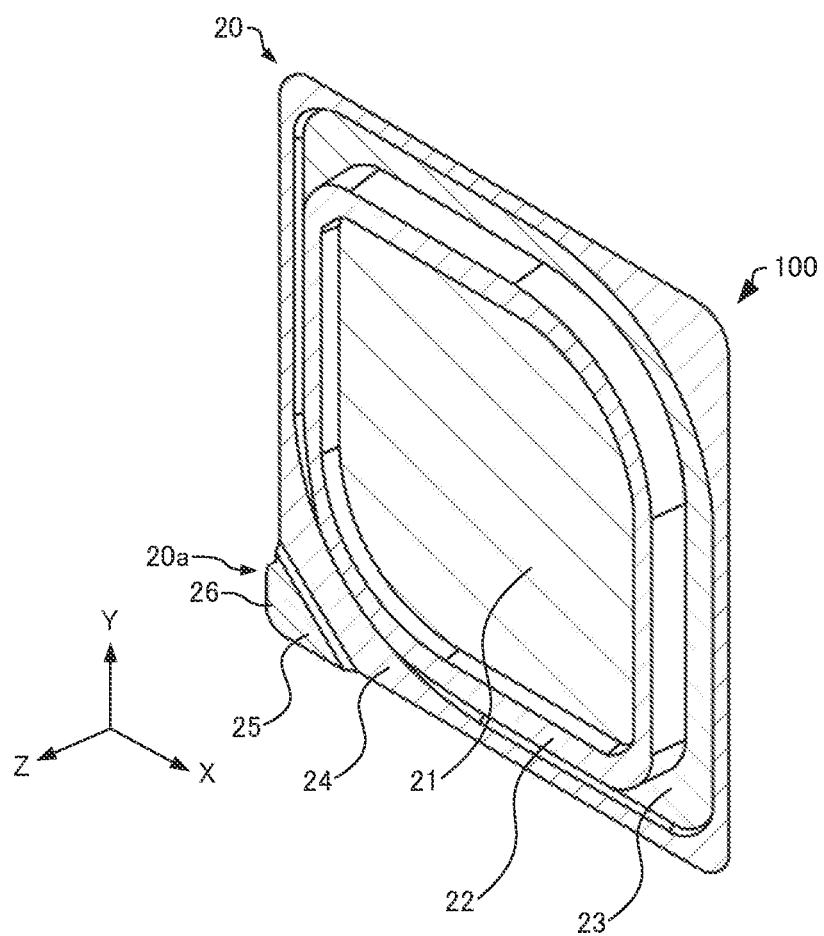
FIG. 5 is a perspective view schematically illustrating the spinal drainage kit container according to the present embodiment.
Figure 6:
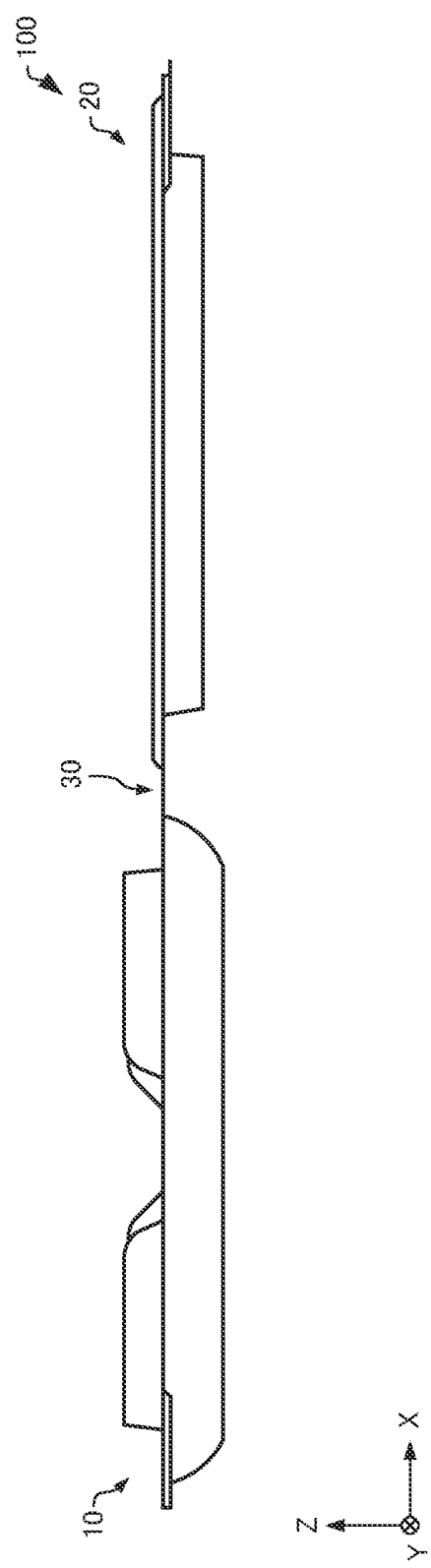
FIG. 6 is a side view schematically illustrating the spinal drainage kit container according to the present embodiment.
Figure 7:
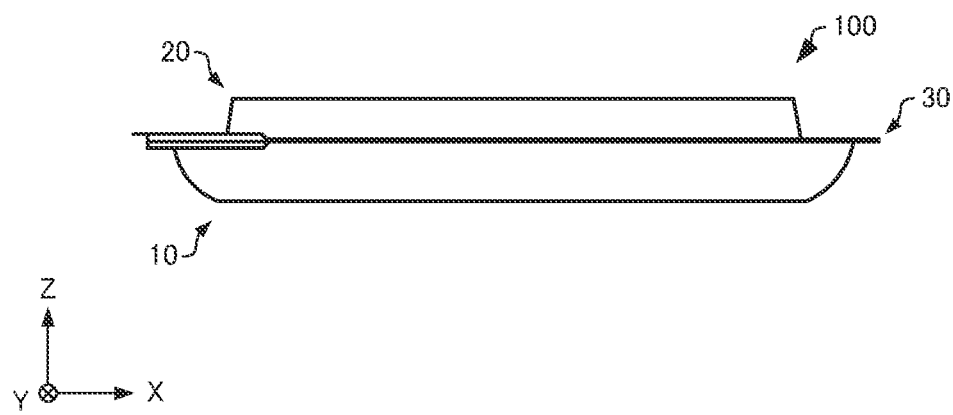
FIG. 7 is a side view schematically illustrating the spinal drainage kit container according to the present embodiment.

A configuration of a spinal drainage kit container according to a present embodiment will be described with reference to the drawings. FIGS. 1 to 3 are plan views schematically illustrating a spinal drainage kit container 100 according to the present embodiment. FIGS. 4 and 5 are perspective views schematically illustrating the spinal drainage kit container 100 according to the present embodiment. FIGS. 6 and 7 are side views schematically illustrating the spinal drainage kit container 100 according to the present embodiment. In FIGS. 1 to 7, an X-axis, a Y-axis, and a Z-axis are illustrated as three axes orthogonal to each other.

As illustrated in FIGS. 1 to 7, the spinal drainage kit container 100 includes a container body 10, a lid 20, and a hinge 30.

FIGS. 1, 2, 4 and 6 illustrate a state where the lid 20 of the spinal drainage kit container 100 is open. Further, FIGS. 3, 5 and 7 illustrate a state where the lid 20 is closed. Furthermore, FIG. 1 illustrates a state where a spinal drainage kit 40 is disposed in the container body 10 of the spinal drainage kit container 100.

A material for the container body 10 is, for example, plastic. Specifically, the material for the container body 10 is, for example, polyethylene terephthalate. The container body 10 is, for example, transparent. The spinal drainage kit container 100 is manufactured, for example, by injection molding.

As illustrated in FIG. 1, the container body 10 is provided with a recessed portion 11. The spinal drainage kit 40 is disposed in the recessed portion 11. The spinal drainage kit 40 includes, for example, a catheter 41, a puncture needle 42, a connector 43, a fixing pad 44, and a fixing seal 45. Here, FIG. 8 is a cross-sectional view taken along an VIII-VIII line in FIG. 2 schematically illustrating the container body 10.

Figure 8:
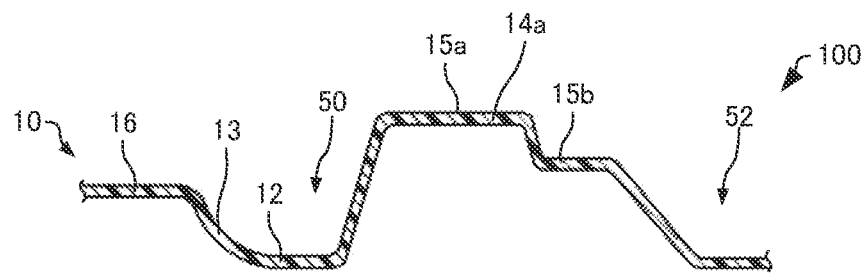
FIG. 8 is a cross-sectional view schematically illustrating the spinal drainage kit container according to the present embodiment.

As illustrated in FIGS. 2 and 8, the container body 10 has a bottom portion 12 and a side portion 13 that define the recessed portion 11. The side portion 13 is connected to an outer periphery of the bottom portion 12. In an example illustrated in FIG. 2, the bottom portion 12 has a plane parallel to an XY plane.

The bottom portion 12 has, for example, a first projecting portion 14a and a second projecting portion 14b. The first projecting portion 14a and the second projecting portion 14b have, for example, high portions 15a and low portions 15b. The height of the high portions 15a in a Z-axis direction is higher than that of the low portions 15b. That is, the high portions 15a are located in a +Z-axis direction relative to the low portions 15b. The height of the low portions 15b in the Z-axis direction is lower than that of the high portions 15a, and is higher than that of the bottom portion 12. In the illustrated example, the high portions 15a and the low portions 15b have planes parallel to the XY plane. The high portions 15a come into contact with a high-portion setting part 22 of the lid 20 in the state where the lid 20 is closed. The low portions 15b do not come into contact with the high-portion setting part 22 of the lid 20 in the state where the lid 20 is closed.

The first projecting portion 14a defines a first chamber 50, a second chamber 52, and a third chamber 54. The catheter 41 is disposed in the first chamber 50. The puncture needle 42 is disposed in the second chamber 52. The connector 43 is disposed in the third chamber 54. In the illustrated example, the fixing pad 44 and the fixing seal 45 are also disposed in the third chamber 54. The first projecting portion 14a is located between the first chamber 50 and the second chamber 52, between the second chamber 52 and the third chamber 54, and between the first chamber 50 and the third chamber 54. The second projecting portion 14b defines the first chamber 50 and the second chamber 52. The second projecting portion 14b is located between the first chamber 50 and the second chamber 52.

The first projecting portion 14a and the second projecting portion 14b define the first chamber 50 so that the first chamber 50 has an annular shape. In a plan view (viewed from the Z-axis direction), the second chamber 52 and the third chamber 54 are surrounded by the first chamber 50.

Figure 9:
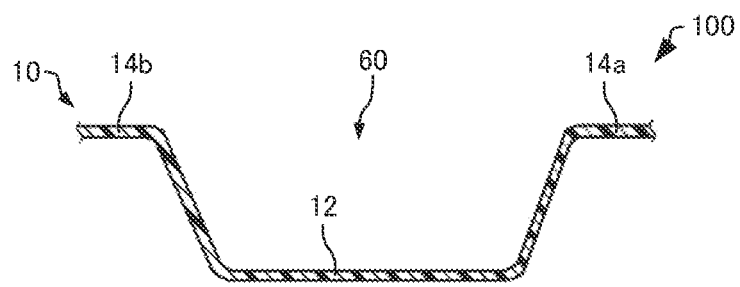
FIG. 9 is a cross-sectional view schematically illustrating the spinal drainage kit container according to the present embodiment.

Here, FIG. 9 is a cross-sectional view taken along a IX-IX line in FIG. 2 schematically illustrating the container body 10.

As illustrated in FIGS. 2 and 9, the first projecting portion 14a and the second projecting portion 14b are separated from each other. The first chamber 50 and the second chamber 52 are connected to each other by first spaces 60 between the first projecting portion 14a and the second projecting portion 14b. As illustrated in FIG. 2, the first projecting portion 14a is configured such that the second chamber 52 and the third chamber 54 are connected to each other by a second space 62. The first chamber 50 and the third chamber 54 are connected to each other through the first spaces 60, the second chamber 52, and the second space 62. As described above, the first chamber 50, the second chamber 52, and the third chamber 54 are connected to each other by the first spaces 60 and the second space 62 regardless of whether the lid 20 is in the state where the lid 20 is closed or the state where the lid 20 is open.

In the illustrated example, in the state where the lid 20 is closed, the first chamber 50, the second chamber 52, and the third chamber 54 are connected to each other not only by the second space 62, but also by third spaces 64 defined by the low portions 15b.

Further, although not illustrated, the bottom portion 12 may have a step. For example, the height of the bottom portion 12 defining the first chamber 50 in the Z-axis direction may be higher than the height of the bottom portion 12 defining the second chamber 52 in the Z-axis direction.

The container body 10 has a peripheral portion 16 and a first grip portion 17. The peripheral portion 16 is provided at a periphery of the recessed portion 11 in plan view. In the illustrated example, the peripheral portion 16 is connected to an end of the side portion 13 in the +Z-axis direction. The peripheral portion 16 is provided so as to surround the recessed portion 11 in plan view. Here, FIG. 10 is a cross-sectional view taken along a X-X line in FIG. 2 schematically illustrating the container body 10.

Figure 10:
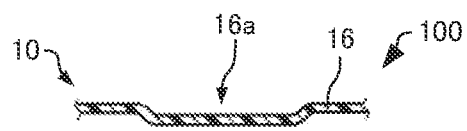
FIG. 10 is a cross-sectional view schematically illustrating the spinal drainage kit container according to the present embodiment.

As illustrated in FIGS. 2 and 10, the peripheral portion 16 is provided with a groove 16a. The groove 16a enables communication between the first chamber 50 and an external space. The first chamber 50 and the external space are connected to each other by the groove 16a regardless of whether the lid 20 is in the state where the lid 20 is closed or the state where the lid 20 is open. In the example illustrated in FIG. 2, the groove 16a is provided at a first corner 10a.

The first grip portion 17 is connected to the peripheral portion 16. The first grip portion 17 is gripped when the lid 20 is to be opened. The first grip portion 17 is provided at the first corner 10a of the container body 10. The first corner 10a is a corner opposite to the hinge 30. In the illustrated example, the first corner 10a is an end of the container body 10 in a −X-axis direction and in a −Y-axis direction. The container body 10 has a substantially rectangular shape. The groove 16a is provided at the first corner 10a. The first grip portion 17 is located in a −Z-axis direction relative to the peripheral portion 16.

The first grip portion 17 has a first protruding portion 18 that protrudes in a first direction. In the example illustrated in FIG. 2, the first protruding portion 18 protrudes in the −Y-axis direction. The first protruding portion 18 does not overlap with the lid 20 in plan view in the state where the lid 20 is closed. That is, the first protruding portion 18 protrudes from the lid 20 in plan view in the state where the lid 20 is closed.

The lid 20 is connected to the container body 10 via the hinge 30. A material for the lid 20 is the same as that for the container body 10. Here, FIG. 11 is a cross-sectional view taken along an XI-XI line in FIG. 2 schematically illustrating the lid 20.

Figure 11:
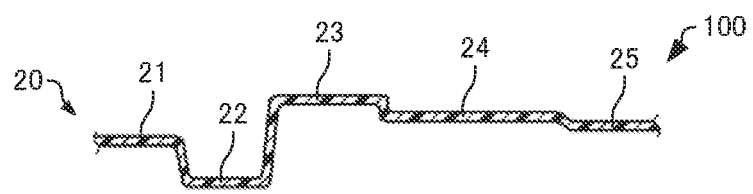
FIG. 11 is a cross-sectional view schematically illustrating the spinal drainage kit container according to the present embodiment.

As illustrated in FIGS. 2 and 11, the lid 20 has a first ceiling portion 21, the high-portion setting part 22, a second ceiling portion 23, a contact portion 24, and a second grip portion 25.

The first ceiling portion 21 defines the second chamber 52 and the third chamber 54 in the state where the lid 20 is closed. The first ceiling portion 21 faces, for example, the bottom portion 12 that defines the second chamber 52 and the third chamber 54.

The high-portion setting part 22 is provided so as to surround the first ceiling portion 21 in plan view. The high portions 15a are disposed at the high-portion setting part 22 in the state where the lid 20 is closed. The high-portion setting part 22 comes into contact with the high portions 15a, for example, in the state where the lid 20 is closed.

The second ceiling portion 23 is provided so as to surround the high-portion setting part 22 in plan view. The second ceiling portion 23 defines the first chamber 50 in the state where the lid 20 is closed. The second ceiling portion 23 faces, for example, the bottom portion 12 that defines the first chamber 50.

The contact portion 24 is provided so as to surround the second ceiling portion 23 in plan view. The contact portion 24 comes into contact with the peripheral portion 16 in the state where the lid 20 is closed.

The second grip portion 25 is connected to the contact portion 24. The second grip portion 25 is gripped when the lid 20 is to be opened. The second grip portion 25 is provided at a second corner 20a of the lid 20. The second corner 20a overlaps with the first corner 10a in plan view in the state where the lid 20 is closed. In the example illustrated in FIG. 2, the second grip portion 25 is located in the −Z-axis direction relative to the contact portion 24. In the state where the lid 20 is closed, the first grip portion 17 and the second grip portion 25 are separated from each other. The groove 16a enables communication between the first chamber 50 and a space between the first grip portion 17 and the second grip portion 25.

The second grip portion 25 has a second protruding portion 26 that protrudes in a second direction. The second direction is a direction orthogonal to the first direction, which is a direction in which the first protruding portion 18 protrudes. In the example illustrated in FIG. 2, the second protruding portion 26 protrudes in a +X-axis direction. The second protruding portion 26 does not overlap with the container body 10 in plan view in the state where the lid 20 is closed. That is, the second protruding portion 26 protrudes from the container body 10 in plan view in the state where the lid 20 is closed.

The hinge 30 connects the container body 10 and the lid 20. The lid 20 is movable about the hinge 30 as a rotation axis. As a result, the spinal drainage kit container 100 can be in the state where the lid 20 is open or the state where the lid 20 is closed. In the illustrated example, the hinge 30 extends in a Y-axis direction.

As illustrated in FIG. 1, the spinal drainage kit container 100 houses, for example, the catheter 41, the puncture needle 42, the connector 43, the fixing pad 44, and the fixing seal 45.

When performing spinal drainage, first, lumbar puncture is performed using the puncture needle 42 that includes an outer needle and a stylet. Next, the stylet is removed from the outer needle of the puncture needle 42, and after confirming an outflow of cerebrospinal fluid, the catheter 41 is introduced into a living body using the outer needle as a guide. The puncture needle 42 is a needle for introducing the catheter 41 into the living body. Next, the outer needle is removed while the catheter 41 is in place in the living body, and the connector 43 is connected to one end of the catheter 41. Then, a drain tube (not illustrated) is connected to the connector 43 to drain the cerebrospinal fluid from the drain tube. The fixing pad 44 and the fixing seal 45 are used to fix the catheter 41.

Although not illustrated, the puncture needle 42 may be housed in the spinal drainage kit container 100 in a state of being housed in a puncture needle container. Further, although not illustrated, the fixing pad 44 and the fixing seal 45 may be housed in the spinal drainage kit container 100 in a state of being housed in a sterilization bag that has been sterilized.

Although not illustrated, the spinal drainage kit container 100 may be housed in a sterilization bag that has been sterilized. The sterilization bag may be filled with sterilization gas. A sterilization treatment may be performed on the spinal drainage kit container 100, and the first chamber 50, the second chamber 52, and the third chamber 54 may be filled with sterilization gas. Examples of the sterilization gas include, for example, ethylene oxide gas, and in this case, the sterilization treatment is an EOG (ethylene oxide gas) sterilization treatment.

The spinal drainage kit container 100 has, for example, the following features.

The spinal drainage kit container 100 includes the container body 10 provided with the recessed portion 11 in which the spinal drainage kit 40 that includes the catheter 41, the puncture needle 42 for introducing the catheter 41 into a living body, and the connector 43 that is connected to the catheter 41 are disposed, the lid 20, and the hinge 30 connecting the container body 10 and the lid 20.

Further, in the spinal drainage kit container 100, the container body 10 includes the peripheral portion 16 provided at the periphery of the recessed portion 11, and the first grip portion 17 that is connected to the peripheral portion 16 and is gripped when the lid 20 is to be opened. The first grip portion 17 is provided at the first corner 10a of the container body 10, which is opposite to the hinge 30. The first grip portion 17 has the first protruding portion 18 protruding in the first direction.

Furthermore, in the spinal drainage kit container 100, the lid 20 includes the contact portion 24 that comes into contact with the peripheral portion 16 in the state where the lid 20 is closed, and the second grip portion 25 that is connected to the contact portion 24 and is gripped when the lid 20 is to be opened. The second grip portion 25 is provided at the second corner 20a that overlaps with the first corner 10a in plan view in the state where the lid 20 is closed. The second grip portion 25 has a second protruding portion 26 that protrudes in a second direction and does not overlap with the container body 10 in plan view in the state where the lid 20 is closed, and the second direction is orthogonal to the first direction.

Therefore, in the spinal drainage kit container 100, the lid 20 can be easily opened as compared with a case where the grip portion does not have a protruding portion. In the spinal drainage kit container 100, for example, by gripping the first protruding portion 18 of the first grip portion 17 with the thumb and index finger of the right hand, and by gripping the second protruding portion 26 of the second grip portion 25 with the thumb and index finger of the left hand, the lid 20 can be opened.

In the spinal drainage kit container 100, the first grip portion 17 and the second grip portion 25 are separated from each other in the state where the lid 20 is closed. Therefore, in the spinal drainage kit container 100, the lid 20 can be easily opened as compared with a case where the first grip portion and the second grip portion are in contact with each other in the state where the lid is closed.

In the spinal drainage kit container 100, the container body 10 has the bottom portion 12 that defines the recessed portion 11. The bottom portion 12 has the first projecting portion 14a that defines the first chamber 50 in which the catheter 41 is disposed, the second chamber 52 in which the puncture needle 42 is disposed, and the third chamber 54 in which the connector 43 is disposed. Therefore, for example, even when carrying the spinal drainage kit container 100 in which the spinal drainage kit 40 is housed, the catheter 41, the puncture needle 42, and the connector 43 can be disposed in the first chamber 50, the second chamber 52, and the third chamber 54, respectively.

In the spinal drainage kit container 100, the second chamber 52 and the third chamber 54 are surrounded by the first chamber 50 in plan view. Therefore, the spinal drainage kit container 100 can be decreased in size as compared with a case where the second chamber and the third chamber are not surrounded by the first chamber in plan view.

In the spinal drainage kit container 100, the first chamber 50, the second chamber 52, and the third chamber 54 are connected to each other, and the groove 16a that enables communication between the first chamber 50 with the external space is provided at the peripheral portion 16. Therefore, in the spinal drainage kit container 100, sterilization gas can be introduced from the groove 16a in the state where the lid 20 is closed, thus the first chamber 50, the second chamber 52, and the third chamber 54 can be filled with the sterilization gas.

In the spinal drainage kit container 100, the groove 16a is provided at the first corner 10a. In the spinal drainage kit container 100, since the first protruding portion 18 is provided at the first corner 10a, the groove 16a serving as an introduction port for the sterilization gas can be easily found.

In the spinal drainage kit container 100, the material for the container body 10 and the lid 20 is plastic. Therefore, the spinal drainage kit container 100 can be formed by injection molding.

The invention is not limited to the above-described embodiments, and various modifications can be made. For example, the invention includes configurations that are substantially the same as the configurations described in the embodiments.

Substantially same configurations means configurations that are the same in function, method, and results, or configurations that are the same in objective and effects, for example. The invention also includes configurations in which non-essential elements described in the embodiments are replaced by other elements. The invention also includes configurations having the same effects as those of the configurations described in the embodiments, or configurations capable of achieving the same objectives as those of the configurations described in the embodiments. The invention further includes configurations obtained by adding known art to the configurations described in the embodiments.

REFERENCE SIGNS LIST

10 Container body
10a First corner
11 Recessed portion
12 Bottom portion
13 Side portion
14a First projecting portion
14b Second projecting portion
15a High portion
15b Low portion
16 Peripheral portion
16a Groove
17 First grip portion
18 First protruding portion
20 Lid
20a Second corner
21 First ceiling portion
22 High-portion setting part
23 Second ceiling portion
24 Contact portion
25 Second grip portion
26 Second protruding portion
30 Hinge
40 Spinal drainage kit
41 Catheter
42 Puncture needle
43 Connector
44 Fixing pad
45 Fixing seal
50 First chamber
52 Second chamber
54 Third chamber
60 First space
62 Second space
64 Third space
100 Spinal drainage kit container

The invention claimed is:

1. A spinal drainage kit container comprising:
a container body including a recessed portion in which a spinal drainage kit is disposed, the spinal drainage kit including a catheter, a puncture needle for introducing the catheter into a living body, and a connector that is connected to the catheter;
a lid; and
a hinge connecting the container body and the lid, wherein:
the container body includes a peripheral portion at a periphery of the recessed portion, and a first grip portion that is connected to the peripheral portion and configured to be gripped when the lid is to be opened;
the first grip portion is at a first corner of the container body, which is opposite to the hinge;
the first grip portion has a first protruding portion that extends away from the first grip portion only in a first direction and does not overlap with the container body in plan view in a state in which the lid is closed;
the lid includes a contact portion that is configured to come into contact with the peripheral portion in the state in which the lid is closed, and a second grip portion that is connected to the contact portion and configured to be gripped when the lid is to be opened;
the second grip portion is at a second corner of the lid, which overlaps with the first corner of the container body in plan view in the state in which the lid is closed;
the second grip portion has a second protruding portion that extends away from the second grip portion only in a second direction and does not overlap with the container body in plan view in the state in which the lid is closed, the second direction being orthogonal to the first direction;

the first grip portion and the second grip portion are separated from each other in the state in which the lid is closed;

the container body has a bottom portion that defines the recessed portion;

the bottom portion has a projecting portion that defines a first chamber in which the catheter is disposed, a second chamber in which the puncture needle is disposed, and a third chamber in which the connector is disposed;

the first chamber, the second chamber, and the third chamber are connected to each other;

a groove that enables communication between the first chamber and an external space is defined at the peripheral portion; and an entirety of the groove overlaps with the lid in plan view in the state in which the lid is closed.

2. The spinal drainage kit container according to claim 1, wherein the second chamber and the third chamber are surrounded by the first chamber in plan view.

3. The spinal drainage kit container according to claim 1, wherein a material for the container body and the lid is plastic.

\* \* \* \* \*